(12) United States Patent
Paspa et al.

(10) Patent No.: US 6,191,931 B1
(45) Date of Patent: Feb. 20, 2001

(54) ALUMINUM ELECTROLYTIC CAPACITOR WITH CONDUCTIVE FEED-THROUGH FOR IMPLANTABLE MEDICAL DEVICE

(75) Inventors: Paul Paspa, San Jose; Craig Mar, Fremont, both of CA (US); Joe Beauvais, Central, SC (US); Kenneth Wong, Sunnyvale, CA (US)

(73) Assignee: Pacesetter, Inc., Sunnyvale, CA (US)

( * ) Notice: Under 35 U.S.C. 154(b), the term of this patent shall be extended for 0 days.

(21) Appl. No.: 09/143,213

(22) Filed: Aug. 28, 1998

(51) Int. Cl.[7] ....................................... H01G 4/35
(52) U.S. Cl. ................... 361/302; 361/508; 607/5
(58) Field of Search .................. 361/302, 306.1, 361/308.3, 328, 508, 517, 528, 532, 541; 607/4, 5, 36, 2

(56) References Cited

U.S. PATENT DOCUMENTS

| | | | |
|---|---|---|---|
| 5,131,388 | * 7/1992 | Pless et al. | 607/5 |
| 5,370,663 | * 12/1994 | Lin | 607/5 |
| 5,522,851 | * 6/1996 | Fayram | 607/5 |
| 5,749,911 | * 5/1998 | Westlund | 607/36 |
| 5,903,109 | * 7/1999 | Fishler | 361/508 |

* cited by examiner

*Primary Examiner*—Kristine Kincaid
*Assistant Examiner*—Anthony Dinkins
(74) *Attorney, Agent, or Firm*—Steven M. Mitchell

(57) ABSTRACT

An electrolytic capacitor with an electrically conductive housing defining a chamber and defining a feed-through aperture providing communication between the interior and exterior of the housing. A number of conductive layers are positioned within the chamber. A feed-through conductor has a first end connected to the layers, an intermediate portion passing through the feed-through aperture, and an elongated external portion extending externally from the housing and terminating at a free end. An insulative sleeve has a first portion closely received within the feed-through aperture and closely receiving the intermediate portion of the feed-through member and has a second elongated portion extending externally from the housing and closely receiving at least a portion of the external portion of the conductor element, so that only a remaining portion of the conductor element is exposed, and is spaced apart from the housing by the length of the second elongated portion.

23 Claims, 5 Drawing Sheets

PRIOR ART

ALUMINUM ELECTROLYTIC CAPACITOR WITH CONDUCTIVE FEED-THROUGH FOR IMPLANTABLE MEDICAL DEVICE

FIELD OF THE INVENTION

This invention relates to electronic components for implantable medical devices, and more particularly to charge storage components for cardiac stimulation devices.

BACKGROUND OF THE INVENTION

Defibrillators are implanted in patients susceptible to cardiac arrhythmias or fibrillation. Such devices provide cardioversion or defibrillation by delivering a high voltage shock to the patient's heart, typically about 500–750V. High voltage capacitors are used in defibrillators to accumulate the high voltage charge following detection of a tachyarrhythmia. In the effort to make implantable devices as small and thin as possible, flat aluminum electrolytic capacitors are used.

Such a flat capacitor is disclosed in U.S. Pat. No. 5,131,388 to Pless et al., which is incorporated herein by reference. Flat capacitors include a plurality of aluminum layers laminarly arranged in a stack. Each layer includes an anode and a cathode, with the anodes and cathodes being commonly connected to respective connectors. The layers may be cut in nearly any shape, to fit within a similarly shaped aluminum housing designed for a particular application. Normally, the cathode layers are together connected to the housing, while the anodes are together connected to a feed-through post that tightly passes through a hole on the housing, but which is electrically insulated from the housing. The feed-through post serves as an external connector for interfacing with other components.

Existing capacitors, such as illustrated in FIG. 1, and disclosed in U.S. patent application Ser. No. 08/876,274, filed Jun. 16, 1997, entitled "Aluminum Electrolytic Capacitor for Implantable Medical Device," now U.S. Pat. No. 5,926,357, which is hereby incorporated by reference, have addressed a trade off in the selection of feed-through 10 materials by using a readily solderable beryllium-copper post 12 passing through an insulated sleeve 14 in the housing 16, and covered within the housing by an aluminum cap 20 to which anode tabs 22 may readily be bonded or welded. A nut 24 is secured externally over the threaded copper post, to draw the cap to compress against an elastomeric gasket 26. This provides an environmental seal that contains electrolyte fluid within the housing, and which prevents the corrosive electrolyte from contacting and attacking the copper post.

While effective, the advantages of such existing capacitor feed-throughs are achieved at a relatively high manufacturing cost, due to their complexity. In addition, part tolerances must be tight, to avoid a condition in which an overly long sleeve engages the post head before the gasket has been adequately compressed. Further, imprecise manufacturing of the cap/post assembly can generate cracks in the cap that may admit corrosive electrolytic fluid to damage the copper post. Also, existing feed-throughs require a foil strip 30 attached to the anode tabs for connection to the feed-through cap, a difficult and time consuming process requiring skillful and precise alignment of the components to be welded. In addition, when more than one capacitor is used in a single device, external jumpers are needed to connect the capacitors together, typically in series. Such jumpers add to the number of parts and to the complexity of manufacturing.

In the prior art device shown in FIG. 1, the nut and adjacent case are sealed with an insulating resin (not shown) to cover the nut 24 and nearby portions of the housing. This normally prevents any arcing between the cathode-connected case and anode connected-nut, which are separated by only a very small gap 32 established by the thickness and radius of the sleeve flange, typically about 0.005–0.010 inch. While arcing is prevented by proper insulation, a minor failure of the insulative coating may generate a serious device failure. Although coating flaws may be detected by careful inspection, a more cost effective method of is desirable. Increasing the sleeve flange thickness would increase the gap, but at a cost of device size, as the post would need to be correspondingly lengthened to provide an adequate free portion for soldering.

SUMMARY OF THE INVENTION

The disclosed embodiment overcomes the limitations of the prior art by providing an electrolytic capacitor with an electrically conductive housing defining a chamber and defining a feed-through aperture providing communication between the interior and exterior of the housing. A number of conductive layers are positioned within the chamber. A feed-through conductor has a first end connected to the layers, an intermediate portion passing through the feed-through aperture, and an elongated external portion extending externally from the housing and terminating at a free end. An insulative sleeve has a first portion closely received within the feed-through aperture and closely receiving the intermediate portion of the feed-through member and has a second elongated portion extending externally from the housing and closely receiving at least a portion of the external portion of the conductor element, so that only a remaining portion of the conductor element is exposed, and is spaced apart from the housing by the length of the second elongated portion. A rigid outer sleeve may be used to fit over the insulative sleeve where it exits the housing to provide strain relief for the insulative sleeve and help maintain seal integrity of the feed-through.

DETAILED DESCRIPTION OF A PREFERRED EMBODIMENT

Figure 1:
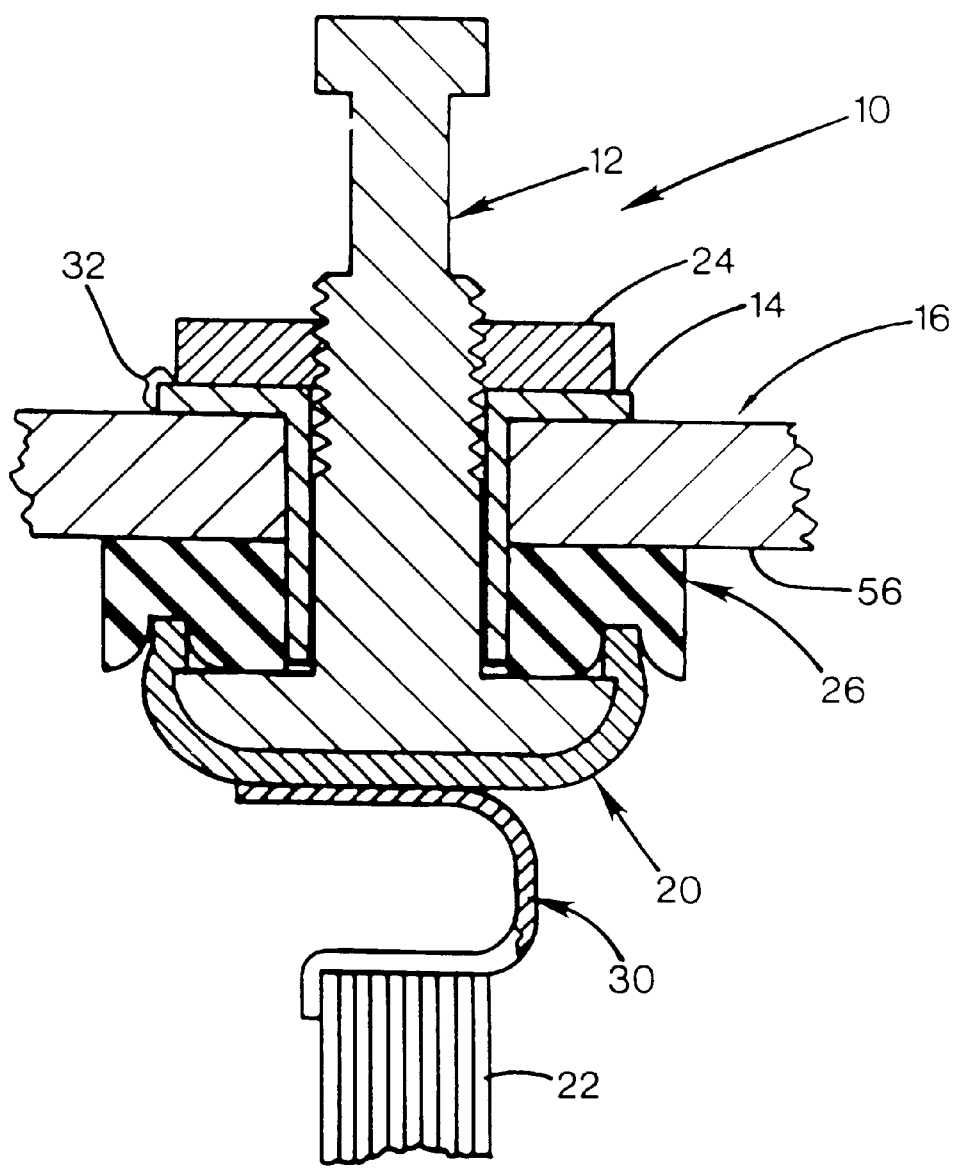
FIG. 1 is an enlarged sectional view of an anode feed-through of a prior art device.
Figure 2:
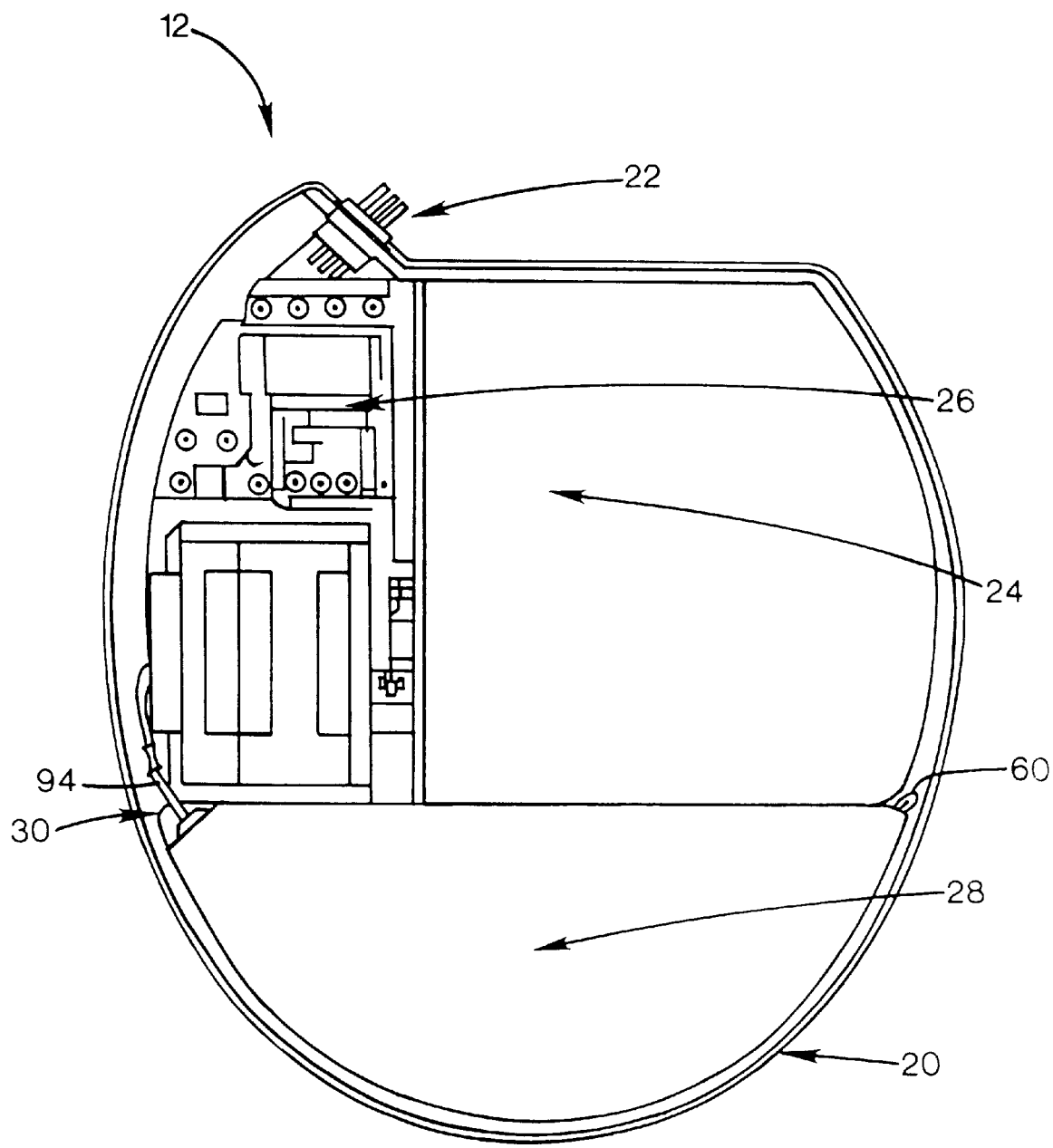
FIG. 2 is a plan view of an implantable medical device according to a preferred embodiment of the invention.

FIG. 2 illustrates a defibrillator 12 for pectoral implantation, with a portion of the housing removed to show interior components. The defibrillator includes an outer housing 20 that includes a lead set feed-through connector 22 for attachment of an endocardial lead set (not shown). The housing 20 contains a battery cell 24, electronic circuitry 26, and a stack of two capacitors 28, 30. The battery provides low voltage electrical energy to a transformer in the circuitry to charge the capacitors so that they may provide a high voltage shock when needed. The circuitry 26 connects to the lead connector so that it may sense and analyze electrical signals from the heart, and control the delivery of an appropriate therapy such as a high voltage shock.

Figure 3:
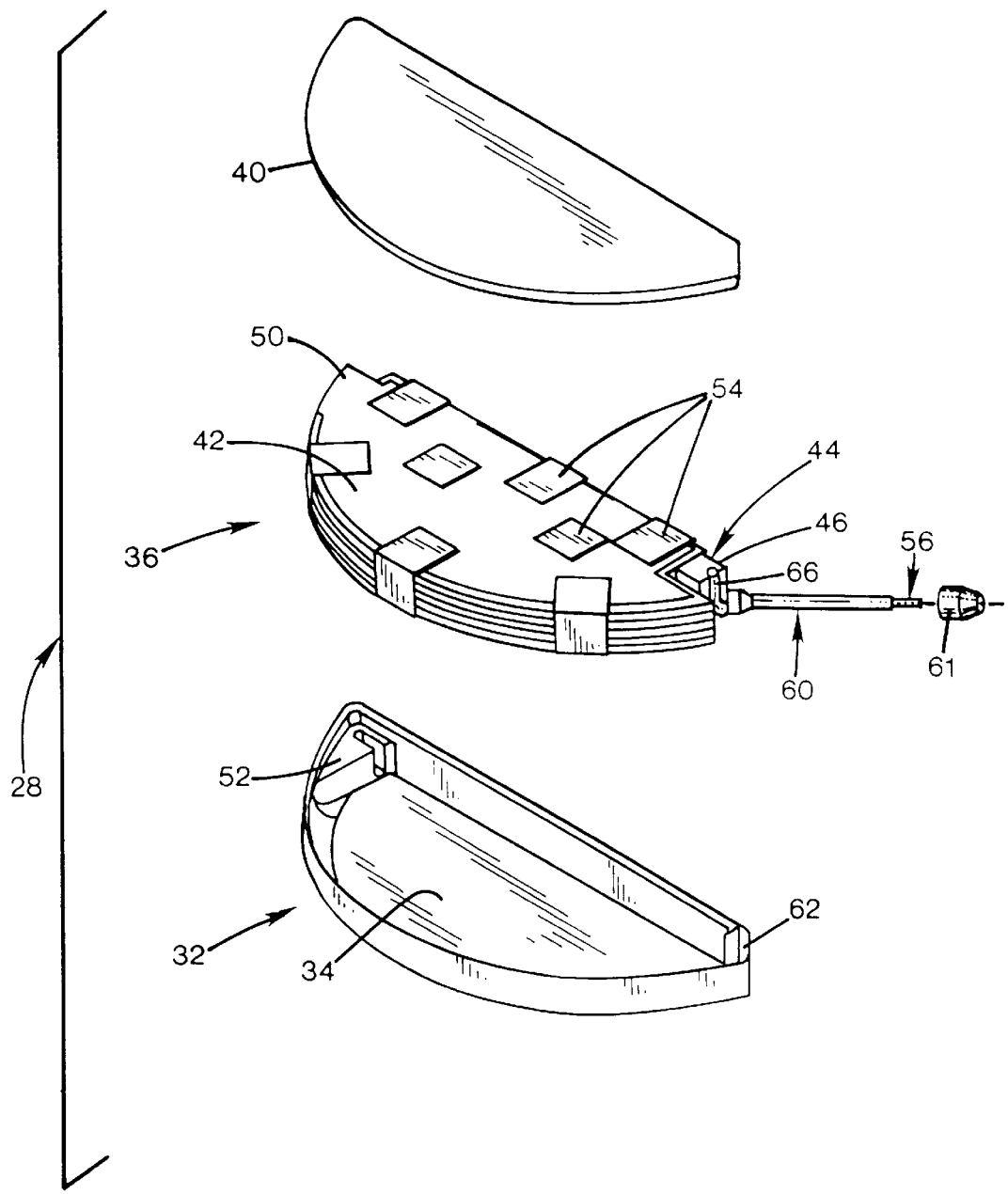
FIG. 3 is an exploded view of a capacitor according to the embodiment of FIG. 2.

FIG. 3 illustrates the capacitor 28, which may be designed as virtually any flat shape to conform to a desired housing shape, and which is identical to capacitor 30. In the preferred embodiment, it is crescent-shaped to conform to a compact, ellipsoidal outer device housing. The capacitor includes an aluminum metallic housing 32 defining a chamber 34, in which resides a capacitor stack 36. The housing includes a lid 40 that encloses the chamber, and which will be welded about the periphery to provide a hermetic seal to retain electrolyte fluid and stack in the chamber.

The capacitor stack 36 is formed of a number of alternating interleaved cathode sheets 42 and anode sheets 44 with insulating separator sheets preventing electrical contact between any anode sheet and any cathode sheet. The anode sheets include anode tabs 46 extending in registration with each other beyond the cathode sheets and separator sheets at one end of the stack 36. Similarly, the cathode sheets include cathode tabs 50 registered with each other for connection to each other and to a step 52 in the housing chamber. The cathodes, like the anodes, are connected together in parallel when the respective tabs are brought together in a bundle. A plurality of tape strips 54 wrap about the edges of the stack at intervals to maintain spacing of the layer edges from the housing walls, and to hold the stack as a unit during manufacturing.

To provide electrical contact to the anodes, a feed-through wire 56 is connected to the anode tabs 46 and extends out of the housing, with an insulative sleeve 60 electrically isolating the wire from the housing. An outer sleeve 61 formed of a rigid plastic such as Delrin is provided to surround the sleeve.

Figure 4:
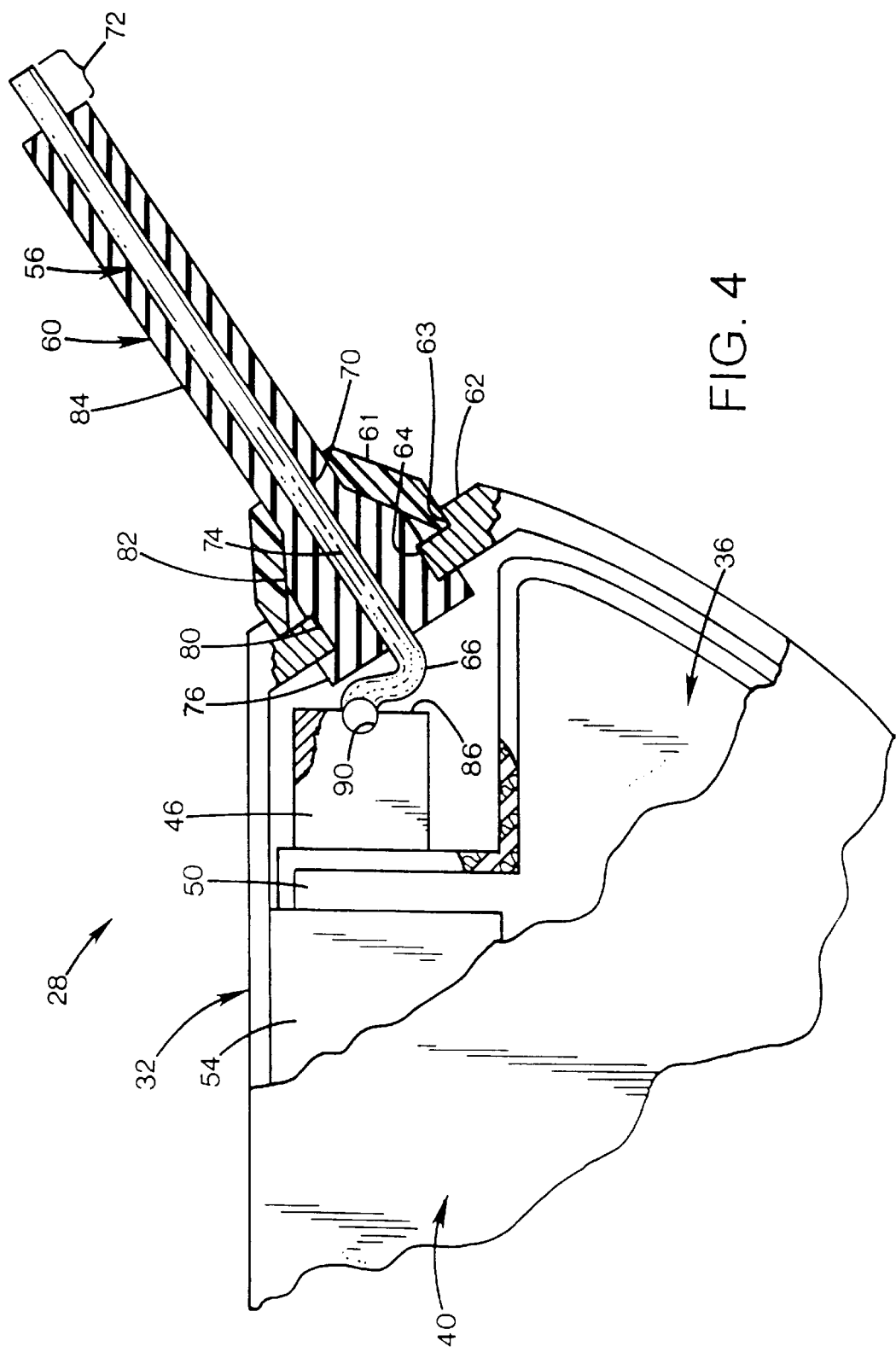
FIG. 4 is an enlarged fragmentary view of a capacitor according to the embodiment of FIG. 2.

As shown in FIG. 4, the housing 32 has a corner wall facet 62 defining a housing aperture 64 that receives the wire and sleeve assembly. The aperture has a counter bore or recess 63 at the exterior of the housing that closely receives part of the outer sleeve 61, which provides strain relief and helps maintain seal integrity for the feed-through. The aperture is electropolished to facilitate assembly and sealing. The wire is a round wire of 1100 Aluminum alloy of 0.0253" diameter, and has an inner end 66 portion extending into the housing, an intermediate portion 70 closely received by the sleeve 60 and passing through the aperture and extending from the housing, and a free end portion 72 extending beyond the sleeve for contact by external circuitry. To provide improved sealing with the sleeve, the wire has an ultrafinish "semi-soft."

The sleeve 60 has a varying circular cross section on a common axis 74 coincident with the axis of the housing aperture and the wire. Beginning at one end, the sleeve includes a flange portion 76 with a diameter greater than the aperture 64, and which rests against the interior surface of the housing wall 62 to provide enhanced sealing. A bushing portion 80 is closely received in the aperture 64, and has a length comparable to the length of the aperture. A tapered shoulder portion 82 has a shoulder that rests against the outer surface of the wall 62, and tapers toward an elongated cylindrical portion 84, which extends well beyond the housing and encloses the majority of the extending wire. The bore of the outer sleeve 61 closely receives the elongated portion, and has a tapered portion that closely receives the tapered portion 82 of the sleeve 60.

The elongated portion 84 of the sleeve 60 has a diameter smaller than the aperture 80, and the tapered shoulder has a diameter only slightly larger the aperture, so that the sleeve (with included wire) may readily be inserted through the aperture from the interior of the housing. The elongated portion presents no resistance, and the tapered portion resists passage only slightly. When inserted, the flange 76 and shoulder 82 will be visibly sealed against the housing wall surfaces.

Figure 5:
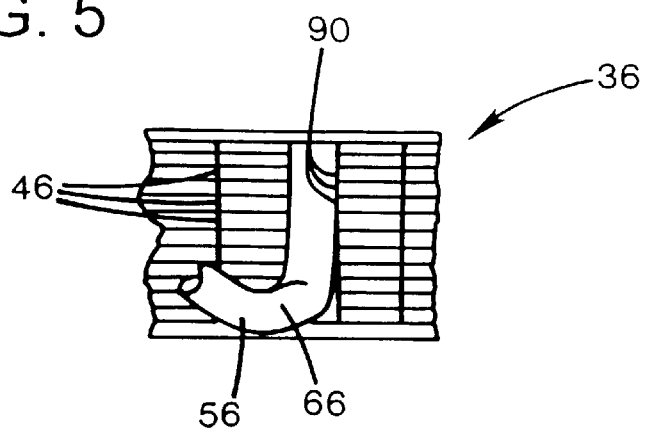
FIG. 5 is an enlarged end view of a capacitor according to the embodiment of FIG. 2.

The anode tabs 46 have an extending free edge 86 extending toward the housing wall 62, and defining a semicircular recess in each tab, so as to define a channel extending perpendicular to the planes of the tabs. As also shown in FIG. 5, the free end of the inner end portion 66 of the wire is press fit into the channel, securing it for laser welding to provide a permanent mechanical and electrical connection, and eliminating the need for clamping the parts to be welded. Normally, a fine wire is difficult to fixture and weld due to its round shape. The channel provides a relatively large area of surface contact to facilitate welding.

In the preferred embodiment, the wire has a total length of 2 inches, with about 1½ inches extending beyond the plane of the outer surface of wall 62, and with the free end portion 72 having a length of 1 inch. This is before the capacitor is connected. When connected, much of the wire's free end may be trimmed when substantial length is not needed (such as connecting to the case of an adjacent serially-connected capacitor as discussed below), or may be insulated by another sleeve when the length is required to connect to more distant circuitry.

While the pure aluminum wire exposed at the free end may be readily contacted by a crimping connector to other circuitry, pure aluminum does not readily make a solder connection. Accordingly, in alternative embodiments where crimp connections are not desired, the free end of the wire may be plated with a solderable material such as nickel or a copper alloy. In either embodiment, the wire remains unplated aluminum where it resides in the chamber, as the electrolyte in the chamber is a solution of ethylene glycol and dodecanoic acid, which would corrode most other conductors or plating materials. Also, the wire must be aluminum for compatibility with the pure aluminum anode sheets to which it is welded.

The housing aperture 64 has a diameter of 0.068 inch, and counterbore 63 has a depth of 0.030 inch.

The sleeve has an overall length of 0.58 inch. The flange 76 has a diameter of 0.106 inch, and a thickness of 0.020 inch. The bushing portion 80 has a length of 0.044 inch and a diameter of 0.079 inch. The bushing portion 80 tapers down to the elongated portion's diameter of 0.040 inch over a length of 0.033 inch. The elongated portion 84 has a length of 0.480 inch, and the inside diameter of the sleeve bore is 0.020 inch, providing a tight interference fit with the wire. The sleeve is preferably manufactured of EPDM elastomer. Suitable alternatives include elastomers such as butyl rubber with less than 5 PPM total free halides.

By insulating a substantial portion of the external length of the wire, the distance between the exposed free end portion of the wire and the cathode-connected housing is great enough to avoid electrical arcing. The flexibility of the sleeve-insulated wire allows it to be bent to conform to the limited space within the capacitor housing 20, and to connect remote conductors.

Figure 6:
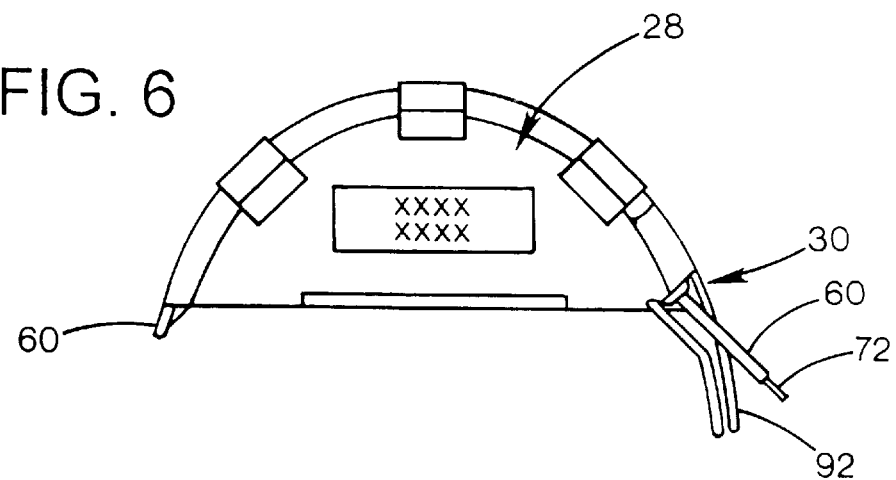
FIG. 6 is a plan view of a capacitor assembly according to the embodiment of FIG. 2.
Figure 7:
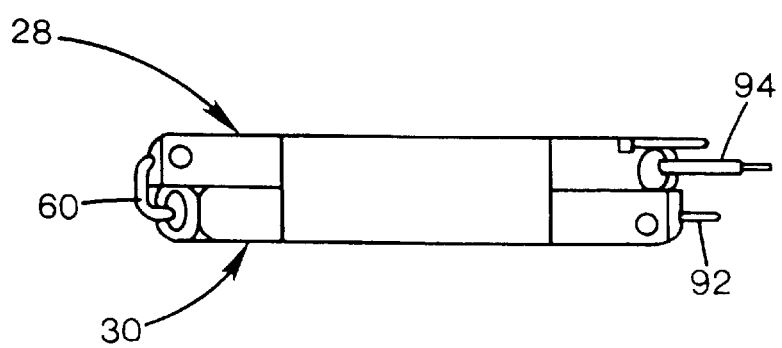
FIG. 7 is a side view of a capacitor assembly according to the embodiment of FIG. 2.

FIGS. 6 and 7 show capacitors 28 and 30 taped together lid-to-lid as an assembly for installation in the capacitor housing, and connected in series electrically. The free end 72 of the wire of capacitor 30 is connected to the housing of capacitor 28, a cathode lead 92 extends from the housing of capacitor 30 at the corner opposite the anode lead, and the wire end portion 72 of capacitor 28 provides an anode lead 94 for the capacitor assembly.

A capacitor is assembled by first assembling the stack of layers. Then, the inner end of the wire is pressed into the tab end groove, which holds it securely for laser welding the wire to the anode tab bundle. This avoids the prior need for an extra foil strip to connect the tabs to each other and to the feed-through conductor. Then, assembly proceeds by one of two approaches. In the preferred embodiment, the sleeve is slipped onto the extending wire, and the sleeved wire is inserted through housing aperture, pulling the free end from the outside the housing. To lubricate the wire for insertion in the sleeve 60, a two-part epoxy such as DP190 from 3M is coated onto the wire. This also provides an enhanced seal by filling any void in the wire or sleeve surfaces. Alternatively, the wire may be lubricated with alcohol for insertion into the sleeve.

The pulling process tends to elongate and narrow the sleeve, allowing the tapered portion to pass through the smaller aperture. Insertion is stopped when the flange 76 rests against the housing wall, and when the entire shoulder of the tapered portion has exited the aperture. An inspection confirms the proper positioning of the shoulder and flange. The counterbore 63 is then filled with additional epoxy, and the outer sleeve 61 placed over the wire and positioned in the counterbore as shown, with the excess epoxy filling any voids between the sleeve 60 and the outer sleeve, and between the outer sleeve and the housing.

In an alternative embodiment process, the sleeve alone is inserted into the housing aperture. Then, the wire is lubricated and inserted into the pre-installed sleeve. Lubrication may be water, alcohol, or a thin epoxy that will cure to provide additional sealing. After the wire and sleeve are in place in either embodiment, the cathode tabs are welded to the housing, the lid is installed and welded to seal the capacitor, and the housing is filled with electrolyte via the fill port.

The two capacitors are then placed lid-to-lid and taped together. One of the anode leads is connected to the housing of the other capacitor, and the assembly is installed in the medical device. The free cathode and anode leads are connected to wires leading to appropriate circuitry, with connections made either by soldering, mechanical crimping, or other appropriate means.

Although the above invention is described in terms of a preferred embodiment, the invention is not intended to be so limited.

What is claimed is:

1. An electrolytic capacitor comprising:
    an electrically conductive housing defining a chamber, and defining a feed-through aperture providing communication with the chamber from outside of the housing;
    a plurality of conductive layers positioned within the chamber;
    a feed-through conductor element having a first end electrically connected to the layers, an intermediate portion passing through the feed-through aperture, and an elongated external portion extending externally from the housing, and terminating at a free end portion; and
    an insulative sleeve having a first portion closely received within the feed-through aperture and closely receiving the intermediate portion of the feed-through conductor element and a second elongated portion extending externally from the housing and closely receiving at least a portion of the external portion of the conductor element, such that only said free end portion of the conductor element is exposed, and is spaced apart from the housing by the length of the second elongated portion.

2. The capacitor of claim 1 further including an outer sleeve fitting over the insulative sleeve and abutting the housing near the aperture.

3. The capacitor of claim 2 wherein the housing includes a counterbore around the aperture and a portion of the outer sleeve abutting the housing is positioned in the counterbore.

4. The capacitor of claim 2 further including an epoxy surrounding a portion of the insulative sleeve at the housing and contacting the outer sleeve to secure the outer sleeve and provide a secondary fluid seal.

5. The capacitor of claim 1 wherein the conductive element is a wire having a circular cross section.

6. The capacitor of claim 1 wherein the conductor element is aluminum.

7. The capacitor of claim 1 wherein the conductor element is formed of a single material.

8. The capacitor of claim 1 wherein the conductor element is connected directly to at least some of the conductive layers.

9. The capacitor of claim 1 wherein at least some of the conductive layers include an edge portion defining a recess, wherein all of the recesses are registered with each other to form a groove, and wherein a portion of the conductor element is received within the groove.

10. The capacitor of claim 1 wherein the insulative sleeve is an elastomer.

11. The capacitor of claim 1 wherein the second elongated portion of the insulative sleeve covers a major portion of the external portion of the conductor element.

12. The capacitor of claim 1 wherein the second elongated portion of the insulative sleeve and the external portion of the conductor element together form a flexible member.

13. An implantable cardiac therapy device comprising:
    a device housing defining a device chamber;
    a plurality of interconnected electronic components positioned within the device chamber;
    a first component comprising an electrolytic capacitor having an electrically conductive capacitor housing defining a capacitor chamber and a feed-through aperture providing communication with the capacitor chamber from outside of the capacitor housing;
    a plurality of conductive layers positioned within the capacitor chamber;
    a feed-through conductor element having a first end electrically connected to the layers, an intermediate portion passing through the feed-through aperture, and an elongated external portion extending externally from the housing, and terminating at a free end portion; and
    an insulative sleeve having a first portion closely received within the feed-through aperture and receiving the intermediate portion of the feed-through conductor element and a second elongated portion extending externally from the housing and closely receiving at least a portion of the external portion of the conductor element, such that only said free end portion of the conductor element is exposed, and is spaced apart from the housing by the length of the second elongated portion.

14. The device of claim 13 wherein the conductor element is a wire having a circular cross section.

15. The device of claim 13 wherein the conductor element is formed of a single material.

16. The device of claim 13 further including an outer sleeve fitting over the insulative sleeve and abutting the capacitor housing near the aperture.

17. The capacitor of claim 13 wherein the capacitor housing includes a counterbore around the aperture and a portion of the outer sleeve abutting the housing is positioned in the counterbore.

18. The capacitor of claim 13 further including an epoxy surrounding a portion of the insulative sleeve at the capacitor housing and contacting the outer sleeve to secure the outer sleeve and provide a secondary fluid seal.

19. The device of claim 13 wherein at least some of the conductive layers include an edge portion defining a recess, wherein all of the recesses are registered with each other to form a groove, and wherein a portion of the conductor element is received within the groove.

20. The device of claim 13 wherein the insulative sleeve is an elastomer.

21. The device of claim 13 wherein the second elongated portion of the insulative sleeve covers a major portion of the external portion of the conductor element.

22. The device of claim 13 wherein the second elongated portion of the insulative sleeve and the external portion of the conductor element together form a flexible member.

23. The device of claim 22 wherein the feed-through aperture defines an axis and the flexible member is angularly disposed from the axis.

* * * * *